United States Patent
Yang

(10) Patent No.: US 10,602,986 B2
(45) Date of Patent: Mar. 31, 2020

(54) FURNITURE ARTICLE WITH USER HEALTH ANALYZING SYSTEM

(71) Applicant: Lei Yang, City of Industry, CA (US)

(72) Inventor: Lei Yang, City of Industry, CA (US)

(73) Assignee: Furniture of America, Inc., City of Industry, CA (US)

( * ) Notice: Subject to any disclaimer, the term of this patent is extended or adjusted under 35 U.S.C. 154(b) by 484 days.

(21) Appl. No.: 14/961,853

(22) Filed: Dec. 7, 2015

(65) Prior Publication Data

US 2017/0160709 A1 Jun. 8, 2017

(51) Int. Cl.
| | | |
|---|---|---|
| *G05B 21/00* | (2006.01) |
| *A61B 5/00* | (2006.01) |
| *G16H 40/63* | (2018.01) |
| *G16H 40/67* | (2018.01) |
| *A61B 5/0205* | (2006.01) |

(52) U.S. Cl.
CPC .............. *A61B 5/6891* (2013.01); *A61B 5/00* (2013.01); *G16H 40/63* (2018.01); *G16H 40/67* (2018.01); *A61B 5/002* (2013.01); *A61B 5/02055* (2013.01); *A61B 2562/046* (2013.01); *A61B 2562/066* (2013.01); *G05B 2219/2642* (2013.01)

(58) Field of Classification Search
CPC ...... G06F 19/3418; A61B 5/00; A61B 5/6891
USPC ........................... 700/275; 705/2, 1.1; 70/275
See application file for complete search history.

(56) References Cited

U.S. PATENT DOCUMENTS

| | | | | |
|---|---|---|---|---|
| 5,410,471 A | * | 4/1995 | Alyfuku ................ | A61B 5/117 4/314 |
| 9,510,688 B2 | * | 12/2016 | Nunn .................... | A47C 27/083 |
| 2008/0077020 A1 | * | 3/2008 | Young .................. | A61B 5/0205 600/484 |
| 2008/0126122 A1 | * | 5/2008 | Warner ................. | G06F 19/327 705/2 |
| 2010/0225489 A1 | * | 9/2010 | Hinterlong ............ | A61B 5/103 340/573.4 |
| 2013/0012786 A1 | * | 1/2013 | Horseman ........... | G06F 19/3418 600/301 |
| 2013/0013327 A1 | * | 1/2013 | Horseman ........... | G06F 19/3418 705/1.1 |
| 2015/0128353 A1 | * | 5/2015 | Kildey .................. | A61M 21/00 5/706 |
| 2015/0258301 A1 | * | 9/2015 | Trivedi ................. | G06F 16/636 600/28 |
| 2015/0355612 A1 | * | 12/2015 | Franceschetti ........ | G16H 40/67 700/275 |
| 2016/0015315 A1 | * | 1/2016 | Auphan ............... | A61B 5/4815 600/301 |
| 2016/0022202 A1 | * | 1/2016 | Peterson ............. | A61B 5/4812 368/251 |
| 2017/0135883 A1 | * | 5/2017 | Franceschetti ........ | A61G 7/018 |

* cited by examiner

*Primary Examiner* — Connie C Yoha
(74) *Attorney, Agent, or Firm* — Raymond Y. Chan; David and Raymond Patent Firm

(57) ABSTRACT

A smart furniture includes a furniture article designed for being used by a user and a smart system which includes a detection module built-in with the furniture article for detecting health data of the user when the furniture article is used. In particular, the detection module includes a plurality of sensors located at a user supporting surface of the furniture article for collecting health data of the user. The health data of the user is then analyzed to ensure the user to use the furniture article in a proper way.

20 Claims, 4 Drawing Sheets

FURNITURE ARTICLE WITH USER HEALTH ANALYZING SYSTEM

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to furniture, and more particularly to a smart furniture, which provides a smart system to collect different health data and evaluate health condition of the users.

Description of Related Arts

Nowadays, people are highly aware of their living environment such that people devoted much enthusiasm for decorating their houses and offices. Furniture, such as mattress, table, desk, chair, and sofa, is necessary and useful article and is considered a form of decorative art. In addition, people will spend most of their times in variety of furniture. For example, people will generally spend eight hours a day for sleeping on a mattress, eight hours a day sitting on a chair in the office, and four hours a day sitting a sofa for watching television. Therefore, using these furniture in an improper way will affect their health.

Researchers have discovered about a good sleep as a key part of healthy lifestyle. An sufficient sleep or disturbed sleep may cause some serious health problems such as heart disease, heart attacks, diabetes, and obesity. Regular periods of sleep enable the body and mind to rejuvenate and rebuild, so that a good life quality is usually built up with the good sleep quality. In order to improve the sleep quality, a suitable mattress is a necessity. A suitable mattress is not only based on the hardness and softness of the mattress, but also ergonomically designed. However, the normal mattress is designed for all common people. Most of people choose a mattress relative to their personal preferences and subjective judgements. They purchase a spring-type mattress which makes them feel comfortable at the time when they tested. However, the spring mattress will rapidly lose its spring support after a period of time. Therefore, memory foam mattresses are widely popular in the current market. The memory foam mattresses are designed to the body in response to the heat and pressure, wherein the memory foam mattresses are adapted for evenly distributing the body weight of the users, changing the hardness and softness of the mattress based on the users' body temperature, and returning to their original form. However, the memory foam mattresses have several drawbacks. The memory foam mattresses retain the body heat, which make the users feel less comfortable in warm weather.

Another example is the office chair, wherein the user will sit on the office chair 8 hours a day. Accordingly, the office chair has an ergonomically design to provide a back support, leg rest, and/or arm support for allowing the user to sit properly. However, the sitting posture or sitting height of the user will change frequently. An improper sitting posture will cause back and joint pain instantly and will require physical therapy after a period of time.

SUMMARY OF THE PRESENT INVENTION

The invention is advantageous in that it provides a smart furniture, wherein a smart system is incorporated with a furniture article for not only collecting health data of the users in a real time manner, but also analyzing the health condition of the users.

Another advantage of the invention is to provide the smart furniture, wherein the smart system comprises a detection module having different kinds of sensors for detecting health parameters of the users.

Another advantage of the invention is to provide the smart furniture, wherein the detection module can generate different kinds of health data, and the health data is transmitted to an analysis module through a data transceiver, and then being processed and analyzed by the analysis module.

Another advantage of the invention is to provide the smart furniture, wherein the analysis module is an application to be installed into an electronic module, such as personal computer, mobile phone, or tablet, such that the user is able to view the health data via the electronic module.

Another advantage of the invention is to provide the smart furniture, wherein the data transceiver comprises a display module to enable the health data display thereon in a real time manner, so as to facilitate the users understanding their health condition immediately.

Another advantage of the invention is to provide the smart furniture, wherein the smart system comprises an adjustor adapted to adjust the pressure or temperature of the furniture article. In other words, the pressure and temperature of the furniture article can be adjusted to match within a predetermined range of the health criteria in a tool-less manner.

Another advantage of the invention is to provide the smart furniture, wherein a comprehensible result is generated by the analysis module after processing and analyzing the health data, such that the user is able to view the comprehensible result and to use the furniture article in an optimized manner.

Another advantage of the invention is to provide the smart furniture which does not require to alter the original structure design of the furniture, so as to easily and immediately detect the health condition of the users.

Another advantage of the invention is to provide the smart furniture, wherein no expansive or complicated structure is required to employ in the present invention in order to achieve the above mentioned advantages. Therefore, the present invention successfully provides an economics and efficient solution for providing the smart system to the smart furniture to detect the health condition of the users without affecting the main structure of the smart furniture.

Additional advantages and features of the invention will become apparent from the description which follows, and may be realized by means of the instrumentalities and combinations particular point out in the appended claims.

According to the present invention, the foregoing and other objects and advantages are attained by a smart furniture, comprising;

a furniture article designed for being used by a user; and a smart system which comprises a detection module built-in with the furniture article for detecting health data of the user when the furniture article is used.

In accordance with another aspect of the invention, the present invention comprises a method of evaluating health condition of a user when a furniture article is used, comprising the following steps executed by a computerized unit.

(A) Collect health data from the user, when the furniture article is used, by a plurality of sensors of a detection module located at different locations of the furniture article.

(B) Analyze the health data by an analysis module.

(C) Generate a comprehensible result in response to the furniture article being used by the user.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Figure 1:
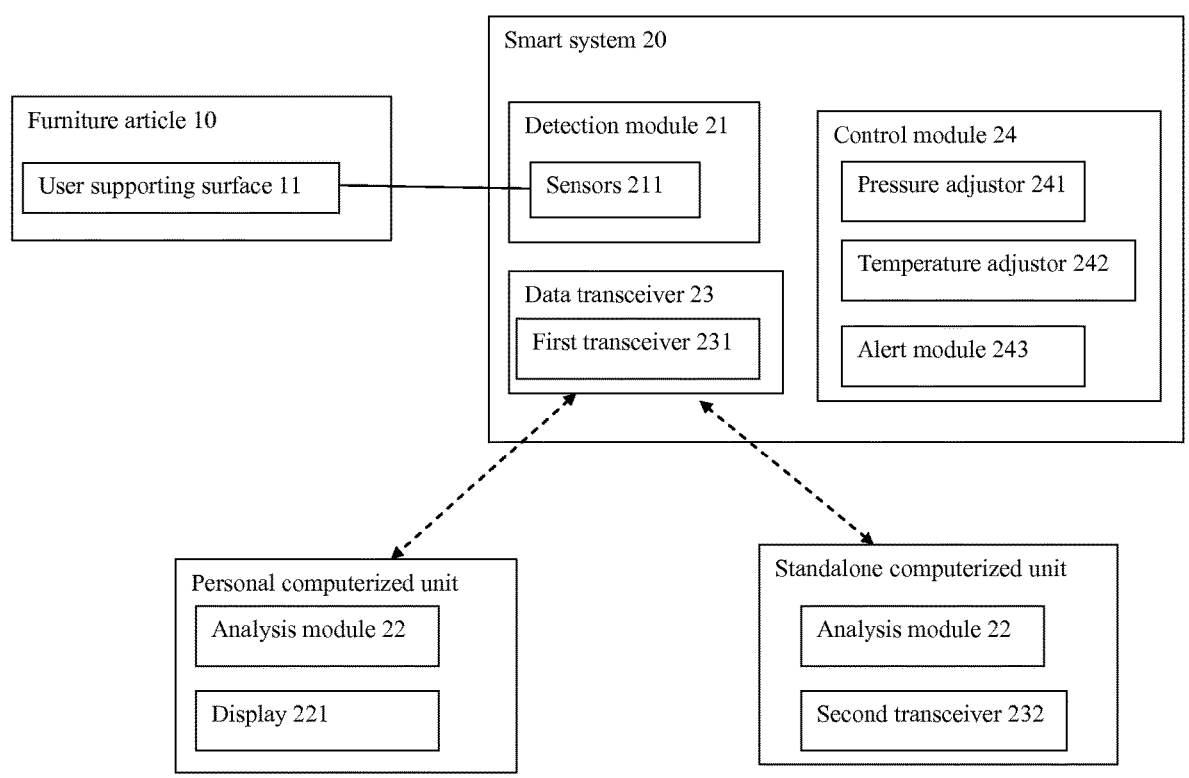
FIG. 1 is a block diagram of furniture with a smart system according to a preferred embodiment of the present invention.

Referring to FIG. 1 of the drawings, a smart furniture according to a preferred embodiment of the present invention is illustrated, wherein the smart furniture comprises a furniture article 10 and a smart system 20 incorporating with the furniture article 10 for providing various kinds of health analyzing function for the furniture article 10. The smart system 20 of the present invention serves as a health monitoring system.

The furniture article 10 is designed for being used by a user. The furniture article 10 can be different kinds of furniture, such as mattress, chair, or sofa. The smart system 20 is adapted to incorporate with the furniture article 10, so that the furniture article 10 not only can be used to monitor the users' health condition, but also can be adjusted to fit body conditions for the individual person, when the furniture article 10 is used. The furniture article 10 can reset to its original settings after the user stops using the furniture article 10. In other words, the furniture article 10 is adequate to different weights, heights, and race of human beings with different kinds of health condition. The user is defined as a person who sleeps on the mattress or a person who sits on the sofa or chair according to the preferred embodiment. Accordingly, the furniture article 10 has a user supporting surface for the user to contact or to support thereon. For example, the top mattress surface of the mattress serves as the user supporting surface of the furniture article 10 or the sitting surface of the sofa/chair serves as the user supporting surface of the furniture article 10.

As shown in FIG. 1, the smart system 20 comprises a detection module 21 for detecting health data of the user when the furniture article 10 is used. In particular, the detection module 21 comprises a plurality of sensors 211 located at different locations of the furniture article 10 for detecting the health data from the user. When different sensors 211 are used, different health data can be collected. In other words, when the furniture article 10 is used by the user, the body condition of the user can be automatically measured by the detection module 21 to generate different kinds of health data. For example, the sensors 211 can be weight sensors, pressure sensors, posture sensors, temperature sensors, respiration sensors, and heart-rate sensors being incorporated with different furniture articles 10.

The smart system 20 further comprises an analysis module 22 operatively linked to the detection module 21 to receive the health data therefrom, wherein the analysis module 22 not only processes and analyzes the health data but also generates a comprehensible result in response to the furniture article 10.

According to the preferred embodiment, the analysis module 22 can be a standalone computerized unit with an analysis software installed thereinto. Preferably, the analysis module 22 can be an application being installed into a personal computerized unit, such as personal computer, mobile phone, and/or tablet, such that the user is able to view the comprehensible result through the personal computerized unit.

Accordingly, after receiving the health data from the detection module 21, the analysis module 22 will process the health data according to the furniture article 10. Depending on the sensors 211 being used on the furniture article 10, different health data will be processed by the analysis module 22. For example, when the posture sensors are used, the analysis module 22 will analyze the posture of the user when the user supports on the user supporting surface 11 of the furniture article 10 to generate the comprehensible result for indicating whether the posture of the user is proper or not. When the temperature sensors are used, the analysis module 22 will analyze the body temperature of the user when the user supports on the user supporting surface 11 of the furniture article 10 to generate the comprehensible result for indicating the body temperature of the user. When the heart-rate sensors are used, the analysis module 22 will analyze the heart rate of the user when the user supports on the user supporting surface 11 of the furniture article 10 to generate the comprehensible result for indicating the heart rate of the user.

The smart system 20 further comprises a data transceiver 23 operatively linked between the detection module 21 and the analysis module 22, wherein the data transceiver 23 is able to receive different kinds of data from the detection module 21, and the different kinds of health data are integrated together as health parameters. The data transceiver 23 comprises a first transceiver 231 operatively linked to the detection module 21 to transmit the health data therefrom.

Accordingly, when the analysis module 22 is the standalone computerized unit, the data transceiver 23 further comprises a second transceiver 232 operatively linked to the analysis module 22, wherein the second transceiver 232 is wirelessly linked to the first transceiver 231, such that the health data from the detection module 21 can be wirelessly transmitted to the analysis module 22 through the first and second transceivers 231, 232. It is appreciated that the first and second transceivers 231, 232 can connected via any data cable. The analysis module 22 further comprises a display 221 for displaying the comprehensible result.

When the analysis module 22 is an application being installed into the personal computerized unit, the analysis module 22 is executed in the personal computerized unit. The personal computerized unit will wirelessly link to the first transceiver 231 in order to receive the health data from therefrom. The comprehensible result will be displayed on the display of the personal computerized unit.

Accordingly, the analysis module 22 processes the health data into comprehensible and explicit charts, figure, or diagrams to facilitate professional evaluate the physical health of the user.

It is worth mentioning that the smart system 20 further comprises a control module 24 operatively linked with the detection module 21 via the data transceiver 23, wherein the control module 24 is adapted to adjust and pre-set body parameters of the furniture article 10.

According to the preferred embodiment, the control module 24 comprises a pressure adjustor 241 and a temperature adjustor 242 located at the user supporting surface of the furniture article 10. The pressure adjustor 241 selectively adjusts a stiffness of the user supporting surface 11 of the furniture article 10. The temperature adjustor 242 selectively adjusts a temperature of the user supporting surface 11 of the furniture article 10.

For example, the pressure distribution of the user supporting surface 11 of the furniture article 10 can be adjusted by the pressure adjustor 241 of the control module 24. Therefore, when the user supports on the user supporting surface 11 of the furniture article 10, the stiffness of the user supporting surface 11 of the furniture article 10 will be adjusted to evenly support the user. In other words, when the body pressure of the user is unbalance on the user supporting surface 11 of the furniture article 10, the pressure distribution of the furniture article 10 is able to be adjusted to support the unbalance condition of the user's body.

The control module 24 is adapted to maintain the body temperature of the user when the furniture article 10 is used, wherein when the body temperature of the user is detected and read lower than the criteria temperature, such as during the winter time, the temperature adjustor 242 of the control module 24 can increase the temperature of the user supporting surface 11 of the furniture article 10 so as to provide a comfortable surface for the user. Likewise, when the body temperature of the user is detected and read higher than the criteria temperature, such as during the summer time, the temperature adjustor 242 of the control module 24 can reduce the temperature of the user supporting surface 11 of the furniture article 10 so as to provide a comfortable surface for the user.

Furthermore, the control module 24 also provides an alert module 243, which provides audio or visible alert signal, to alert the user while the bodies parameters of the user are exceed the criteria. The user is able to input any health condition, disease or symptom in the analysis module 22. For example, when the body posture of the user is detected and read as an improper posture, the alert module 243 of the control module 24 will generate the alert signal so as to remind the user to use the furniture article 10 properly. The alert module 243 further provides an alarm function to generate an alarm signal to remind the user. For example, the alarm module 243 can be set by the user as a wake up alarm for waking up the user and/or a reminder alarm for reminding the user to take a break after the furniture article 10 is used for a period of time usage. It is worth mentioning that the alert module 243 can be built-in with the standalone computerized unit and/or the personal computerized unit.

Figure 2:
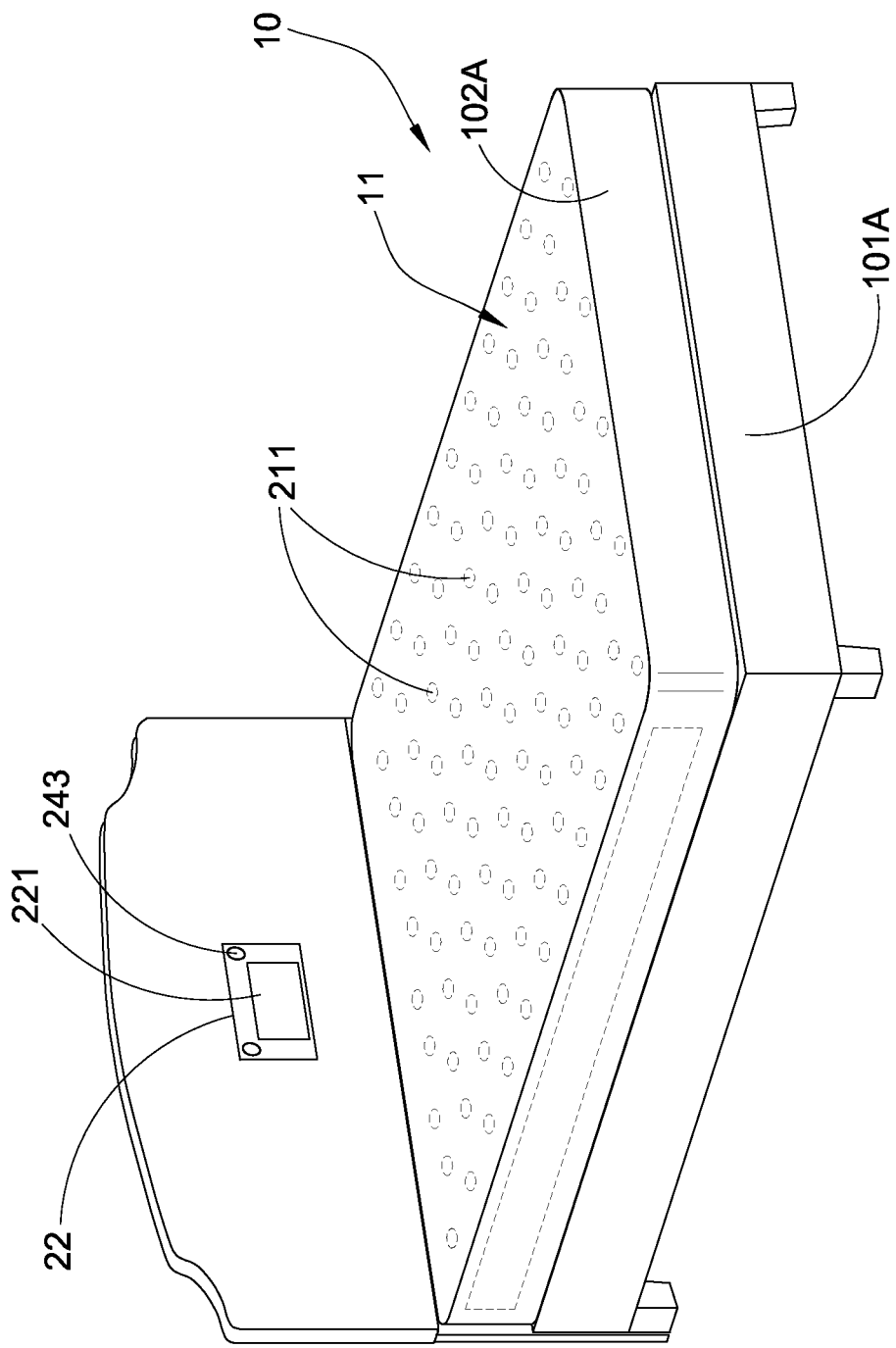
FIG. 2 is a perspective view of the furniture according to the above preferred embodiment of the present invention, illustrating the furniture article as a bed frame.

FIG. 2 illustrates the furniture article 10 as a bed frame which comprises a bed support 101A and a mattress 102A, wherein the user supporting surface 11 of the furniture article 10 defines on a top mattress surface of the mattress. The smart system 20 will detect and analyze the current sleeping quality of the user, and improve the sleeping quality. Accordingly, the sensors 211 are located at different locations of the user supporting surface 11 of the furniture article 10 for detecting the health data from the user. The sensors 211 should include weight sensors, pressure sensors, posture sensors, temperature sensors, respiration sensors, and heart-rate sensors. All different health data from different sensors 211 will be collected and sent to the analysis module 22 for analysis. Therefore, the user is able to view different health data in the comprehensible result.

One or more weight sensors will collect the weight of the user when the user sleeps on the top mattress surface of the mattress 102A. Accordingly, the control module 24 will adjust the stiffness of the top mattress surface of the mattress 102A according to the weight of the user. In other words, for heavy user, the stiffness of the top mattress surface of the mattress 102A will be increased manually or automatically to provide sufficient support for the user. For light user, the stiffness of the top mattress surface of the mattress 102A will be reduced manually or automatically to provide comfortable support for the user.

One or more pressure sensors will collect data of different body pressures of the user when the user sleeps on the top mattress surface of the mattress 102A. The pressure sensor is adapted to measure the pressure distribution of the user's body to generate a pressure data, wherein the pressure date comprises the strength distribution of the pressure applied on the top mattress surface of the mattress 102A and the frequency change of the pressure thereon. The pressure data is collected by and transmitted from the detection module 21 to the analysis module 22 through the data transceiver 23. After the pressure data is transmitted from the detection module 21, the pressure date is processed by the analysis module 232. As a result, the pressure data can be represented as different types of diagrams, such as the pressure relative to the time, the pressure relative to the position, and the pressure strength relative to the time or/and position, such that the user/professional can understand the pressure distribution condition of the user while they are sleeping on the mattress 102A.

One or more posture sensors will collect the data of sleeping postures of the user when the user sleeps on the top mattress surface of the mattress 102A. Accordingly, the sleeping posture of the user will change during sleeping. The data of sleeping postures will be collected and analyzed to effectively prevent the rachiopathy or other kinds of body sore.

One or more temperature sensors will collect the body temperature of the user when the user sleeps on the top mattress surface of the mattress 102A. The temperature sensor is adapted to measure the temperature of the user's body in a real time manner to generate a temperature data, wherein the temperature data comprises the body temperature in a real time manner of the user and the ambient temperature. The temperature change during sleeping will be collected and analyzed to determine the sleeping quality of the user. According to the temperature data, the control module 24 will provide a comfortable sleeping zone for the user to improve the sleeping quality. For example, the top mattress surface of the mattress 102A will be warm up when the body temperature of the user drops below a preset temperature threshold to prevent the user catching cold. Likewise, the top mattress surface of the mattress 102A will be cooled when the body temperature of the user increases above a preset temperature threshold to prevent the user waking up by the heat. In other words, the temperature adjustor 242 of the control module 24 will provide a thermostatic top mattress surface of the mattress 102A for the user sleeping thereon.

One or more respiration sensors will collect the respiration rate of the user when the user sleeps on the top mattress surface of the mattress 102A. The respiration sensor is adapted to measure the respiration rate of the user's body within a period of sleeping time to generate a respiration data, so that the respiration rate of the user can be evaluated by the respiration sensor. In other words, the respiration data can be used to evaluate the snore condition of the users since most of people don't know that they are snoring while they are sleeping. In addition, the respiration date also can be used to evaluate respiratory diseases.

One or more heart-rate sensors will collect the heart rate of the user when the user sleeps on the top mattress surface of the mattress 102A. The heart-rate sensor is adapted to detect the heart rate of the user to generate a heart-rate data. Normally, the heart-rate during sleeping is lower than the heart-rate during the normal activities. Therefore, if the heart-rate of the user increases during sleeping, some kinds of heart diseases can be diagnosed, such as myocardial ischemia or cardiac dysfunction, which are not easy to be discovered in an early stage, so that the heart-rate data can support the user to receive timely treatment.

It is worth mentioning that the smart system 20 can detect and analyze two users sleeping on the top mattress surface of the mattress 102A. In other words, two sets of health data will be collected and analyzed at the same time.

In addition, the alert module 243 of the control module 243 will generate the alert signal in case of emergency. For example, the user who has heart attack symptom can be input into the analysis module 22. Therefore, when the detection module 21 detects any shortness of breath and/or breaking out in a cold sweat of the user, the alert module 243 of the control module 243 will generate the alert signal to the user and/or to the emergency institution, such as police station or hospital.

The alarm module 243 can be preset by the user to wake up the user. Accordingly, the health data is collected from the detection module 21 and is analyzed by the analysis module 22 to determine the sleeping cycle of the user. In other words, the smart system of the present invention will track the sleep patterns of the user. The health data will be analyzed to determine a light sleep phase, a deep sleep phase, and dream phase via the sensors, such as the posture sensors and pressure sensors to track the movement on the user supporting surface 11 of the furniture article 10. Therefore, the alarm module 243 will generate the alarm signal to wake up the user during the light sleep phase. For example, the user is able to set the alarm time between 7:00 am and 7:30 am. The alarm module 243 will generate the alarm signal to wake up the user during the light sleep phase between 7:00 am and 7:30 am.

It is worth mentioning that the furniture article 10 can be embodied as an inflatable mattress, and the pressure adjustor 241 is adapted to adjust the pressure distribution of the inflatable mattress. In other words, the pressure adjustor 241 is activated to adjust the air distribution of the inflatable mattress so as to evenly distribute the pressure of the users applied on the inflatable mattress. In addition, the furniture article 10 also can be embodied as an inflatable pad which can be incorporated with any kinds of mattress, so that the inflatable pad can be covered on the top portion of the mattress to form the user supporting surface 11 on the inflatable pad to achieve the above mentioned function.

Figure 3:
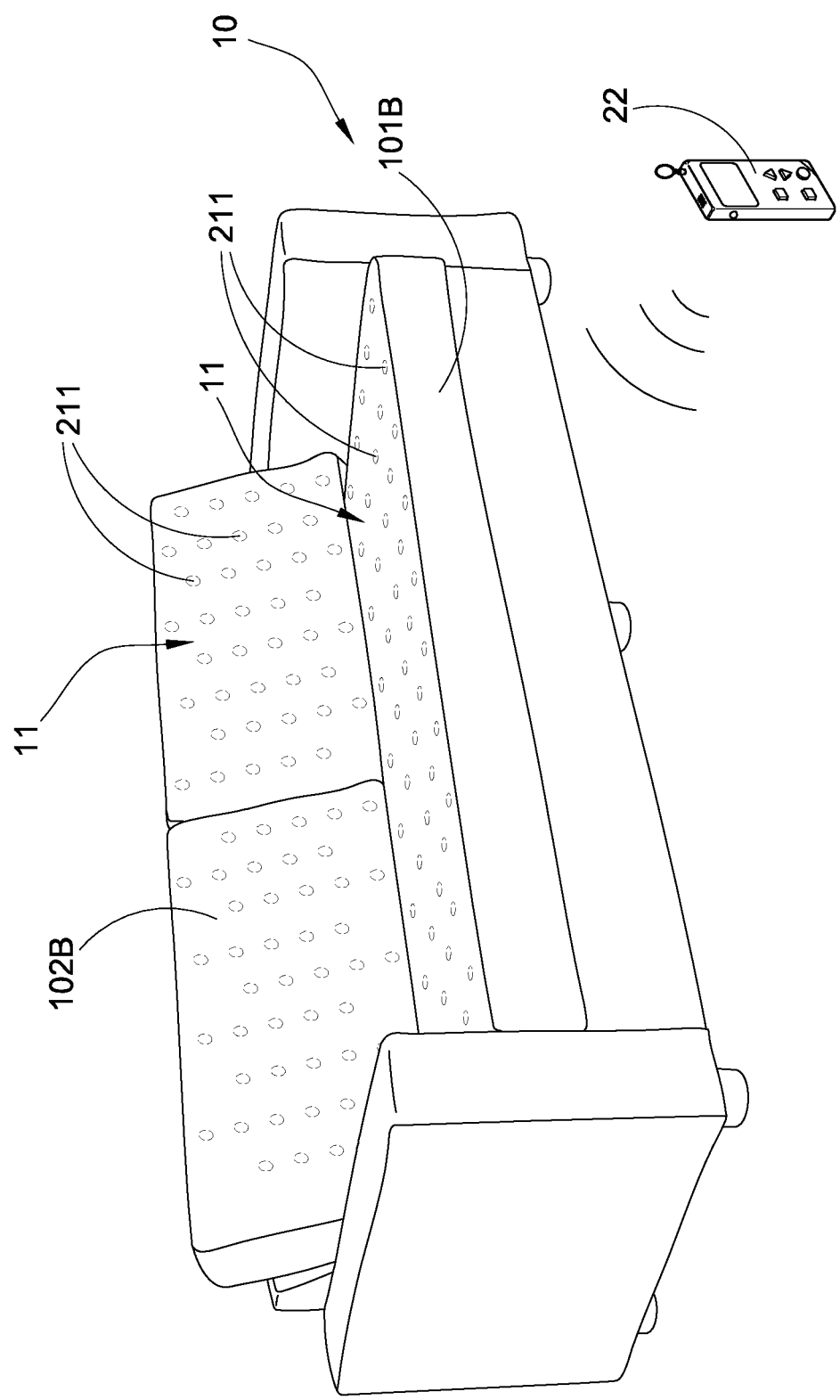
FIG. 3 is a perspective view of the furniture according to the above preferred embodiment of the present invention, illustrating the furniture article as a sofa.

FIG. 3 illustrates the furniture article 10 as a sofa which comprises a seat frame 101B and a back support frame 102B, wherein the user supporting surface 11 of the furniture article 10 defines on a sitting surface of the seat frame 101B and the back supporting surface of the back support frame 102B. The smart system 20 will detect and analyze the current sitting posture of the user, and improve the sitting posture. Likewise, the sensors 211 are located at different locations of the user supporting surface 11 of the furniture article 10 for detecting the health data from the user. The sensors 211 should include weight sensors, pressure sensors, posture sensors, temperature sensors, respiration sensors, and heart-rate sensors. All different health data from different sensors 211 will be collected and sent to the analysis module 22 for analysis. Therefore, the user is able to view different health data in the comprehensible result.

It is worth mentioning that the alert module 243 will generate a reminder alarm for reminding the user to stand up after sitting on the sofa for a period of time usage. In addition, the smart system 20 can detect and analyze different users sitting on the sofa. For example, the smart system 20 can selectively adjust different stiffness levels at different sitting areas of the sofa to provide sufficient supports for different users with different weights.

Figure 4:
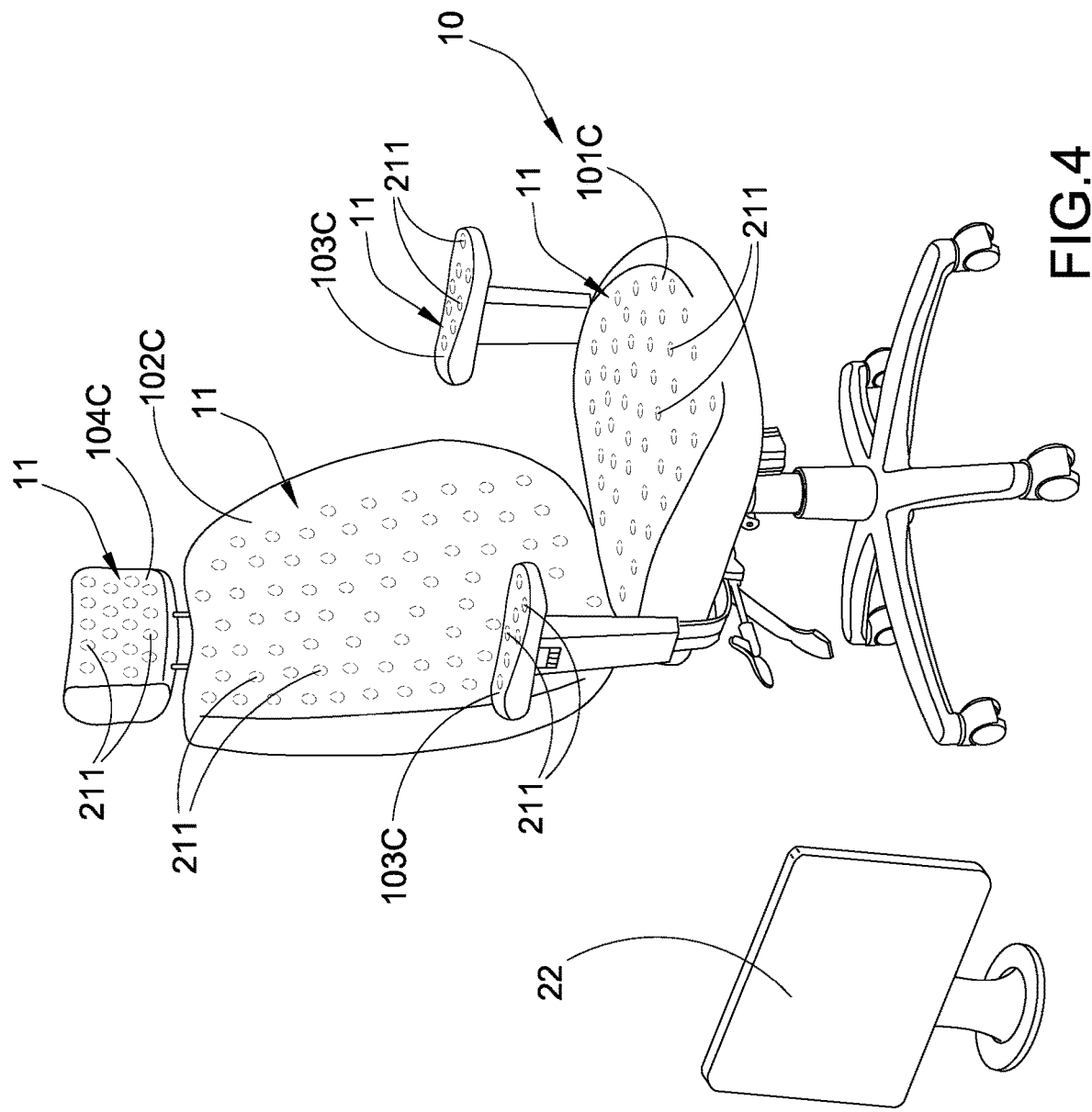
FIG. 4 is a perspective view of the furniture according to the above preferred embodiment of the present invention, illustrating the furniture article as a chair.

FIG. 4 illustrates the furniture article 10 as a chair, i.e. the office chair, which comprises a sit support 101C, a back support 102C, an arm rest support 103C, and/or a head rest support 104C, wherein the user supporting surface 11 of the furniture article 10 defines on a chair surface of the chair, including the supporting surfaces of the sit support 101C, the back support 102C, the arm rest support 103C, and/or the head rest support 104C. The smart system 20 will detect and analyze the current sitting posture of the user, and improve the sitting posture. Likewise, the sensors 211 are located at different locations of the user supporting surface 11 of the furniture article 10 for detecting the health data from the user. The sensors 211 should include weight sensors, pressure sensors, posture sensors, temperature sensors, respiration sensors, and heart-rate sensors. All different health data from different sensors 211 will be collected and sent to the analysis module 22 for analysis. Therefore, the user is able to view different health data in the comprehensible result.

Especially for the posture sensors, the head, back, and arm postures of the user will be detected. The analysis module 22 will analysis the sitting posture of the user. A bad sitting posture and/or sitting too long on the chair will increase the risk of cardiovascular disease and worsen back pain. Then, the control module 24 will remind and alert the user in response to the sitting posture and sitting time to prevent any problem, such as numbness, spinal misalignment, joint pain, neck pain, and/or herniated discs. In other words, the control module 24 will adjust the body parameters of the chair to provide sufficient support for the user sitting thereon.

Therefore, when the furniture article 10 is used, the smart system 20 of the present invention will monitor the health of the user by collecting the health data of the user, analyze the health condition of the user by analyzing the health data, and ensure the user to use the furniture article 10 in a comfortable and proper way by selectively adjusting the body parameters of the furniture article 10.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A smart furniture, comprising:
 a furniture article designed for being used by a user, wherein said furniture article has a user supporting surface for the user contacting and supporting thereon; and
 a smart system which comprises a detection module built-in with said user supporting surface of said furniture article for detecting health data of the user when said furniture article is used, wherein said detection module comprises a plurality of different sensors built-in with said user supporting surface of said furniture article; wherein said smart system further comprises an analysis module and a control module, wherein said detection module is operatively linked with said analysis module and said control module, wherein said analysis module analyzes health data to determine a light sleep phase, a deep sleep phase, and a dream phase; wherein said control module further comprises an alert module, wherein said alert module generates an alarm signal at a preset alarm time range to wake up the user during the light sleep phase, wherein one of said sensors is a pressure sensor, and one of said sensor is a posture sensor that tracks a movement on said user supporting surface of said furniture article to determine the light sleep phase, such that in response to said posture sensor, said alarm signal is generated at said preset alarm time range by said alert module when said posture sensor detects the light sleep phase of the user.

2. The smart furniture, as recited in claim 1, wherein two of said sensors are a weight sensor collecting a weight data of the user and a respiration sensor collecting a respiration data of the user.

3. The smart furniture, as recited in claim 2, wherein, in response to said weight sensor, said control module further comprises a pressure adjustor that selectively adjusts a stiffness of said user supporting surface of said furniture article according to a body pressure of the user applied thereon so as to ensure a balance support of said user supporting surface of said furniture article.

4. The smart furniture, as recited in claim 1, wherein said analysis module not only processes and analyzes said health data but also generates a comprehensible result in response to said furniture article.

5. The smart furniture, as recited in claim 3, wherein said analysis module not only processes and analyzes said health data but also generates a comprehensible result in response to said furniture article.

6. The smart furniture, as recited in claim 4, wherein said analysis module is an application being installed into a computerized unit.

7. The smart furniture, as recited in claim 5, wherein said analysis module is an application being installed into a computerized unit.

8. The smart furniture, as recited in claim 4, wherein said smart system further comprises a data transceiver wirelessly linking said detection module with said analysis module to wirelessly transmit said health data from said detection module to said analysis module.

9. The smart furniture, as recited in claim 5, wherein said smart system further comprises a data transceiver wirelessly linking said detection module with said analysis module to wirelessly transmit said health data from said detection module to said analysis module.

10. The smart furniture, as recited in claim 1, wherein said smart system further comprises a control module built-in with said furniture article to adjust body parameters of said furniture article.

11. The smart furniture, as recited in claim 1, wherein said smart system further comprises a control module built-in with said furniture article to adjust body parameters of said furniture article.

12. The smart furniture, as recited in claim 10, wherein one of said sensors is a temperature sensor collecting data of body temperature of the user, wherein said control module comprises a temperature adjustor located at said user supporting surface of said furniture article, wherein, in response to said temperature sensor, said temperature adjustor selectively adjusts a temperature of said user supporting surface of said furniture article.

13. The smart furniture, as recited in claim 11, wherein one of said sensors is a temperature sensor collecting data of body temperature of the user, wherein said control module comprises a temperature adjustor located at said user supporting surface of said furniture article, wherein, in response to said temperature sensor, said temperature adjustor selectively adjusts a temperature of said user supporting surface of said furniture article.

14. A method of evaluating health condition of a user when a furniture articles is used, comprising the steps executed by a computerized unit of:
 (a) collecting health data from the user, when the furniture article is used, by a plurality of sensors of a detection module located of different locations of a user supporting surface of said furniture article that said user supporting surface thereof is configured for contacting and supporting the user, wherein the step (a) comprises a step of:
 (a.1) tracking a movement on said user supporting surface of said furniture article via a posture sensor;
 (b) analyzing said health data to determine a light sleep phase, a deep sleep phase, and a dream phase by an analysis module which is a computerized unit, wherein said light sleep phase is determined when said wherein said posture sensor tracks the movement on said user supporting surface of said furniture article; and
 (c) in response to said posture sensor, generating an alarm signal at a preset alarm time range by an alert module for waking up the user during the light sleep phase.

15. The method, as recited in claim 14, wherein the step (a) further comprises the steps of:
 (a.2) collecting a weight data of the user via a weight sensor on said user supporting surface of said furniture article; and
 (a.3) collecting a respiration data of the user via a respiration sensor when the user supports on said user supporting surface of said furniture article.

16. The method, as recited in claim 15, wherein said sensors are temperature sensors and heart-rate sensors.

17. The method, as recited in claim 15, wherein said health data from said detection module wirelessly transmitted to said analysis module.

18. The method, as recited in claim 15, wherein the step (b) further comprises a step of installing said analysis module as an application into personal computerized unit.

19. The method, as recited in claim 15, further comprising a step of adjusting body parameters of said furniture article via a control module built-in with said furniture article, wherein the adjusting step comprises the steps of selectively adjusting a stiffness of said user supporting surface of said furniture article via a pressure adjustor in response to said weight sensor, and selectively adjusting a temperature of said user supporting surface of said furniture article via a temperature adjustor in response to a temperature sensor that detects a body temperature of the user on said user supporting surface of said furniture article.

20. The method, as recited in claim 19, wherein said pressure adjustor and said temperature adjustor are located at said user supporting surface of said furniture article.

\* \* \* \* \*